(12) United States Patent
Manzo et al.

(10) Patent No.: US 12,257,012 B2
(45) Date of Patent: Mar. 25, 2025

(54) SURGICAL INSTRUMENT WITH RETAINING FEATURE FOR CUTTING ELEMENT

(71) Applicant: INTUITIVE SURGICAL OPERATIONS, INC., Sunnyvale, CA (US)

(72) Inventors: Scott E. Manzo, Shelton, CT (US); Ralph Wadensweiler, Sunnyvale, CA (US); Ben Schoettgen, Los Gatos, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 562 days.

(21) Appl. No.: 17/697,560

(22) Filed: Mar. 17, 2022

(65) Prior Publication Data
US 2022/0202513 A1 Jun. 30, 2022

Related U.S. Application Data

(62) Division of application No. 16/338,793, filed as application No. PCT/US2017/054740 on Oct. 2, 2017, now Pat. No. 11,291,513.
(Continued)

(51) Int. Cl.
*A61B 17/295* (2006.01)
*A61B 17/00* (2006.01)
(Continued)

(52) U.S. Cl.
CPC ........ *A61B 34/35* (2016.02); *A61B 17/00234* (2013.01); *A61B 17/295* (2013.01);
(Continued)

(58) Field of Classification Search
CPC ............ A61B 17/00234; A61B 17/295; A61B 2017/00477; A61B 2034/305; A61B 18/1445
See application file for complete search history.

(56) References Cited

U.S. PATENT DOCUMENTS 8,241,282 B2  8/2012  Unger et al.
9,055,961 B2  6/2015  Manzo et al.
(Continued)

FOREIGN PATENT DOCUMENTS

WO   WO-2006062555 A2   6/2006

OTHER PUBLICATIONS

International Search Report and Written Opinion for Application No. PCT/US2017/054740, mailed on Jan. 17, 2018, 15 pages.
(Continued)

*Primary Examiner* — Tuan V Nguyen
(74) *Attorney, Agent, or Firm* — JONES ROBB, PLLC

(57) ABSTRACT

A surgical instrument comprises a pair of jaw members comprising a first jaw member comprising a groove along a length portion of the first jaw member, the groove extending from a gripping surface of the first jaw member in a first direction, and a slot along the length portion of the first jaw member and extending from the groove in a second direction, the second direction being different than the first direction. The instrument further comprises a cutting element comprising a first edge engaged with the groove and translatable along the groove; and a retaining feature coupled to the first edge of the cutting element and engaged with the slot, the retaining feature remains engaged with the slot throughout a range of translation of the cutting element. The cutting element is translatable along the groove independently from a movement of the pair of jaw members between open and closed positions.

20 Claims, 11 Drawing Sheets

Related U.S. Application Data

(60) Provisional application No. 62/403,459, filed on Oct. 3, 2016.

(51) Int. Cl.
*A61B 18/14* (2006.01)
*A61B 34/30* (2016.01)
*A61B 34/35* (2016.01)
*A61B 18/00* (2006.01)
*A61B 90/00* (2016.01)

(52) U.S. Cl.
CPC .......... *A61B 18/1445* (2013.01); *A61B 34/30* (2016.02); *A61B 2017/00477* (2013.01); *A61B 2018/00577* (2013.01); *A61B 2018/00601* (2013.01); *A61B 2018/1455* (2013.01); *A61B 2034/305* (2016.02); *A61B 90/36* (2016.02)

(56) References Cited

U.S. PATENT DOCUMENTS

| | | |
|---|---|---|
| 11,291,513 B2 | 4/2022 | Manzo et al. |
| 2003/0055424 A1* | 3/2003 | Ciarrocca .......... A61B 18/1445 606/51 |
| 2012/0078248 A1 | 3/2012 | Worrell et al. |
| 2013/0296843 A1 | 11/2013 | Boudreaux et al. |
| 2014/0142574 A1 | 5/2014 | Heard |

OTHER PUBLICATIONS

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

\* cited by examiner

SURGICAL INSTRUMENT WITH RETAINING FEATURE FOR CUTTING ELEMENT

CROSS REFERENCE TO RELATED APPLICATIONS

This application is a divisional of U.S. application Ser. No. 16/338,793, filed as a U.S. national stage application under 35 U.S.C. § 371(c) of International Application No. PCT/US2017/054740, filed Oct. 2, 2017, which claims priority to U.S. Application No. 62/403,459, filed Oct. 3, 2016 (now expired), each of which is hereby incorporated by reference in its entirety.

TECHNICAL FIELD

Aspects of the present disclosure relate to surgical instruments, and related systems, devices, and methods, that have an end effector component with a translatable cutting element.

INTRODUCTION

The benefits of minimally invasive (e.g., laparoscopic, thoracoscopic, teleoperated, etc.) surgery are known. Instruments for such surgery typically have a surgical end effector mounted at the distal end of a relatively long shaft that is inserted through an opening (e.g., body wall incision, natural orifice) to reach a surgical site. In some cases, the surgical instruments can be passed through a cannula and an endoscope can be used to provide images of the surgical site. In some cases, an articulating wrist mechanism may be mounted at the instrument's distal end to support the end effector and change its orientation with reference to the shaft's longitudinal axis. In some cases, remotely controlled surgical instruments, including both manual, laparoscopic instruments and computer-assisted, teleoperated surgical instruments (sometimes referred to as robotic surgical instruments), are often used in minimally invasive medical procedures. For example, in teleoperated surgical systems, surgeons manipulate input devices at a surgeon console, and those "master" inputs are passed to a patient side cart that interfaces with one or more remotely controlled surgical instruments coupled to the patient side cart. Based on the surgeon inputs at the surgeon console, the one or more remotely controlled surgical instruments are actuated at the patient side cart to operate on the patient, thereby creating a master-slave control relationship between the surgeon console and the surgical instrument(s) at the patient side cart.

Although minimally invasive surgical instruments can include end effectors configured to provide a variety of functionality common to surgical procedures (e.g., forceps, spatula, needle drivers, surgical blades, grippers, electrical energy delivery, suction/irrigation, etc.). One configuration of a surgical instrument end effector comprises a combination of gripping jaw members and a retractable cutting element such as a translating knife or cutting blade. The jaw members may be configured to open and close over a range of motion, thereby being usable to grip a material such as tissue between the gripping jaw members. Optionally, the jaw members may further be provided with electrode surfaces configured to deliver electrosurgical energy, for example to fuse tissue, with the cutting element being used to cut the fused tissue. When combined with a cutting element, gripping jaw members generally include grooves for guiding a translatable cutting element. The cutting element can be translated or moved from a relatively proximal position of the jaw members to a relatively distal position proximate a free end of the jaw members.

Such grooves do not receive or house the edges of the cutting element over a full range of motion of the jaw members, but rather only over a range of motion between a fully closed position and an intermediate position of gripping, i.e. not in a fully open position. For instance, in normal use, the jaw members are closed over a material such as tissue, the cutting element is deployed forward along the grooves, such that a front-facing or distal-facing blade cuts the material. The cutting element is then retracted proximally back into a home position (or "garaged") without slipping out of the grooves. However, when gripping jaw members are in a position between the fully open position and the engaged intermediate gripping position, the retractable cutting element in existing surgical instruments is not constrained in any way. For example, if the jaw members are gripping a larger material such as a tissue bundle or are otherwise in a sufficiently open position, the cutting element can slip out of its track, and be derailed, or a drive component of the cutting element can be bent out of shape. The cutting element also is prone to slipping out of its track(s) when it encounters dry or calcified tissue, or any other hard object such as a staple, colostomy/colpotomy ring, etc. The resultant increased pressure causes a drive element of the cutting element to bend and change an angle of orientation of the cutting element, which can derail the cutting element from the track. This hinders the ability of the cutting element to smoothly translate, for example, such that the cutting element does not return into a home position. Further, regardless of the position of the gripping jaw members, the cutting element can slip out of its tracks when it encounters dry or calcified tissue due to, for instance, increased pressure that causes a drive element of the cutting element to bend and change an angle of the cutting element.

Consequently, it is desirable to improve the functioning of surgical instruments that incorporate cutting elements that translate between jaw members of an end effector. In addition, size constraints pose challenges in the design of surgical instruments for minimally invasive applications. Thus, it is desirable to minimize the size of such instruments without negatively impacting the ability of the instrument to perform multiple functions that may require space to accommodate various actuation and other components along the instrument. There exists a continued need to improve upon electrical flux delivery instruments, such as electrosurgical instruments, and related systems and methods for performing electrosurgical procedures on materials such as tissue.

SUMMARY

Exemplary embodiments of the present disclosure may solve one or more of the above-mentioned technical challenges and/or may demonstrate one or more of the above-mentioned desirable features. Other features and/or advantages may become apparent from the description that follows.

In accordance with at least one exemplary embodiment, the present disclosure contemplates a surgical instrument, comprising a shaft having a proximal end and a distal end, and an end effector coupled to the distal end of the shaft. The end effector comprises a pair of jaw members, each jaw member being configured to be moved relative to the other jaw member between an open position and a closed position, and a cutting element. The jaw members are configured to grip material between gripping surfaces of the jaw members, and the cutting element is configured to cut the material gripped between the gripping surfaces. The cutting element is further configured to translate between and along a lengthwise direction of the jaw members. The cutting element and a first jaw member comprise complementary retaining features that cooperate to retain the cutting element in a position held by the first jaw member throughout a range of motion of the jaw members between the open and the closed position.

In various exemplary embodiments, the complementary retaining features include a retaining flange coupled to the cutting element and a slot provided in a gripping surface of the first jaw member. The slot is configured to house the retaining flange.

In various exemplary embodiments, the retaining flange is oriented at a perpendicular angle to a plane of the cutting element. The gripping surface of the first jaw member may further comprise a first groove oriented with the plane of the cutting element, and the slot is provided within the first groove and is oriented with the retaining flange. Further, the slot and the first groove may run in the lengthwise direction. The slot retains the cutting element in the position held by the jaw member as the cutting element translates along the lengthwise direction.

In various exemplary embodiments, a gripping surface of the second jaw member is provided with a second groove running in the lengthwise direction. The second groove is configured to engage a portion of the cutting element while the jaw members are in the closed position.

In another exemplary embodiment, the portion of the cutting element engaged by the second groove while the jaws are in the closed position is disengaged from the second groove as the jaws are moved towards the open position.

In accordance with another exemplary embodiment, the present disclosure contemplates a surgical instrument, comprising a pair of jaw members configured to grip material. At least one jaw member of the pair of jaw members comprises a groove running along a length of a gripping surface of the at least one jaw member. A planar cutting element is oriented along the length and between the pair of jaw members. A first edge of the planar cutting element is configured to engage the groove. A retaining feature is coupled to the first edge of the planar cutting element, and configured to engage a corresponding slot provided within the groove. The retaining feature remains engaged with the corresponding slot as the cutting element is translated along the length of the gripping surface.

In yet other exemplary embodiments, the pair of jaw members is coupled to a wrist at a proximal end of the pair of jaw members, the wrist being configured to articulate in multiple degrees of freedom about a longitudinal axis. The surgical instrument may further include a cutting element drive component disposed along the longitudinal axis, the cutting element drive component being configured to translate the cutting element along the groove. The cutting element drive component is sufficiently flexible so as to bend as the wrist is articulated in the multiple degrees of freedom about the longitudinal axis and as the at least one jaw member is articulated between an open position and a closed position.

In a various exemplary embodiments, the cutting element drive component is coupled to a second edge of the cutting element, the second edge oriented between the pair of jaw members. A third edge of the cutting element opposite the second edge comprises a sharp edge for cutting the material gripped between the gripping surfaces as the cutting element is translated.

In yet other exemplary embodiments, the retaining feature and the cutting element are molded from a single material. Alternatively, the retaining feature is coupled to the cutting element, and may comprise a pin.

In another exemplary embodiment, each jaw member of the pair of jaw members is configured to be moved from an open position to a closed position independently from the other jaw member.

In accordance with another exemplary embodiment, the present disclosure contemplates a method, comprising gripping a material between opposing surfaces of a pair of jaw members, with each jaw member being configured to be moved relative to each other between open and closed positions, and translating a cutting element provided between the opposing surfaces along a lengthwise direction of the jaw members to cut the material gripped between the opposing surfaces. The cutting element and a first jaw member of the pair of jaw members comprise complementary retaining features that cooperate to retain the cutting element in a position held by the first jaw member throughout a range of motion of the jaw members between the open and the closed position.

Additional objects, features, and/or advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are exemplary and explanatory only and are not restrictive of the claims; rather the claims should be entitled to their full breadth of scope, including equivalents.

BRIEF DESCRIPTION OF THE DRAWINGS

The present disclosure can be understood from the following detailed description, either alone or together with the accompanying drawings. The drawings are included to provide a further understanding of the present disclosure, and are incorporated in and constitute a part of this specification. The drawings illustrate one or more exemplary embodiments of the present teachings and together with the description serve to explain certain principles and operation.

DETAILED DESCRIPTION

Figure 1:
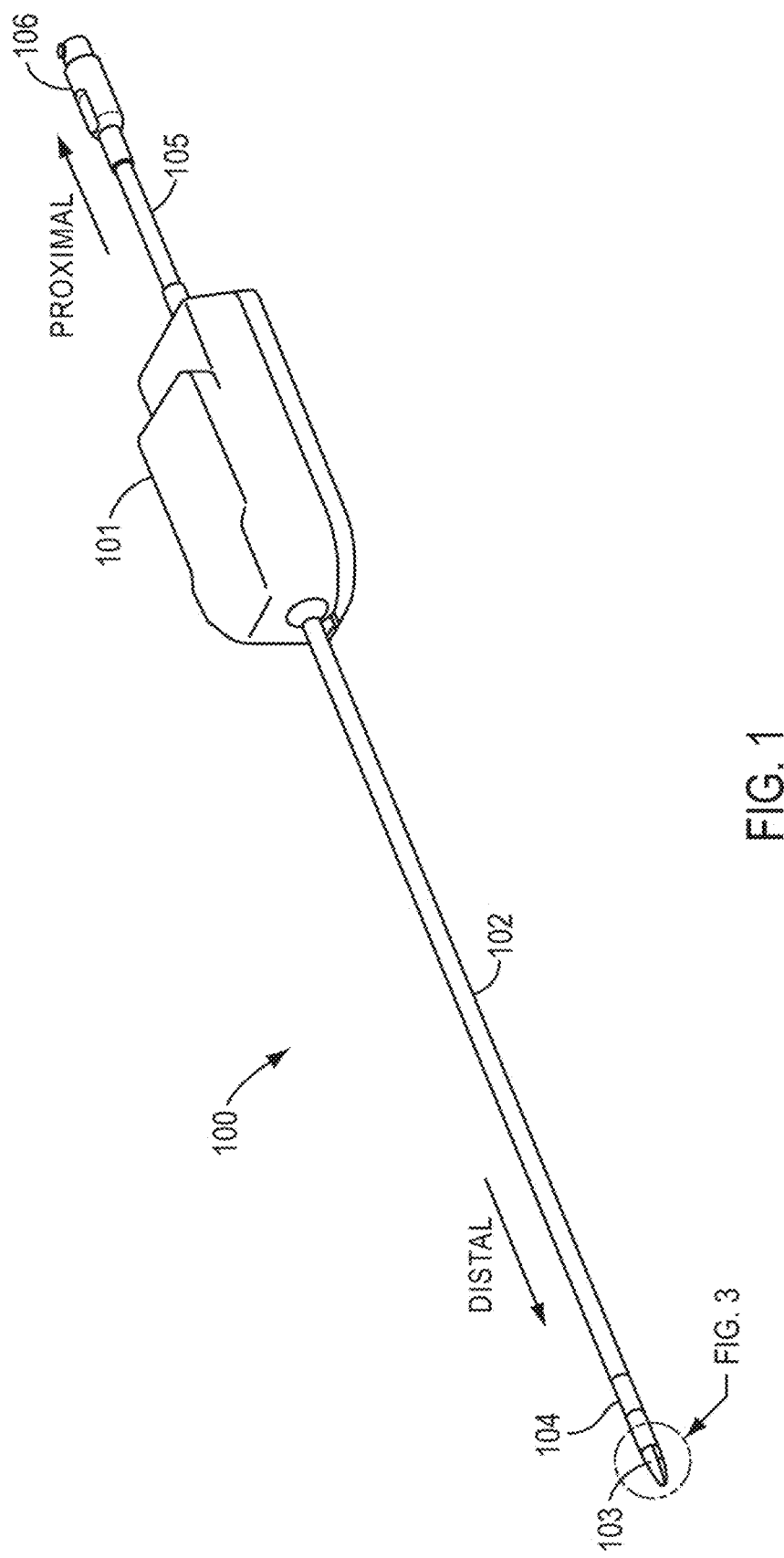
FIG. 1 shows a perspective view of an exemplary embodiment of a minimally invasive surgical instrument.

This description and the accompanying drawings that illustrate exemplary embodiments should not be taken as limiting. Various mechanical, compositional, structural, electrical, and operational changes may be made without departing from the scope of this description and the claims, including equivalents. In some instances, well-known structures and techniques have not been shown or described in detail so as not to obscure the disclosure. Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

In accordance with various exemplary embodiments, the present disclosure contemplates surgical instruments comprising end effectors having a slot that provides a guide and retention track that is configured to receive a portion of a cutting element as it translates during deployment and retraction of the cutting element, thereby preventing the cutting element from slipping out of its desired position within the track. The end effector may comprise, for instance, a pair of opposing jaw members that are configured to grip tissue between the jaw members. For example, in some embodiments, the jaw members may further be configured to deliver electrical energy to perform electrosurgical procedures such as sealing (cauterizing) a material, such as tissue, gripped between gripping surfaces of the pair of jaw members. A retractable cutting element, such as a surgical knife or blade, may be deployed, i.e. translated in a direction along a length of the pair of jaw members for cutting the gripped material (which may have been sealed in the case of an electrosurgical instrument). A retaining feature can be coupled to the cutting element, and at least one jaw member of the pair of jaw members can comprise a complementary retaining feature configured to capture the retaining feature coupled to the cutting element, while the cutting element is translated.

The complementary retaining feature runs along a portion of the length of the at least one jaw member, and can be configured to capture the retaining feature coupled to the cutting element while the jaw members are in any position relative to each other, i.e. between a fully closed position and a fully open position. In other words, the retaining feature presents a stop for preventing the cutting element from being removed from the slot in the at least one jaw member. The retaining feature, and corresponding complementary retaining feature, may be oriented to extend at an angle relative to a plane of the cutting element. For instance, the cutting element may be generally planar in a plane oriented in a lengthwise direction of the jaw members. The plane may further extend between the jaw members such that opposing edges of the plane of the cutting element are respectively proximate the opposing jaw members, with a sharp edge of the cutting element extending between the opposing edges. In an exemplary embodiment, the retaining feature may be coupled proximate to one or both opposing edges of the cutting element. The retaining feature and complementary retaining feature can be angled relative to the plane of the cutting element and the groove forming a track along a surface of the at least one jaw member to guide the translating cutting element. In this way, the complementary retaining feature of the at least one jaw member can receive the retaining feature coupled to the cutting element, and hold the cutting element in position in the track as the jaw members move between the opened and closed position throughout their full range of motion.

Thus, in addition to the groove in the gripping surface that provides a track to receive the opposing edge of the cutting element during its course of deployment/retraction, the at least one jaw member further includes a negative feature (recess, slot, etc.) within a body of the jaw that opens to the groove and is configured to house the retaining feature on the cutting element, so as to maintain a retained configuration of the cutting element with the jaw member. In an exemplary embodiment, the complementary retaining feature of the jaw member can be sized to accommodate the retaining feature and a portion of the cutting element, as well as to allow for some movement of the cutting element in a direction of the plane of the cutting element and toward the opposing jaw member. In various exemplary embodiments, the arrangement of the retaining feature coupled to the cutting element and the complementary retaining feature of the jaw member permits a substantial amount of the entire sharp edge of the cutting element to be exposed, in order to sufficiently cut tissue throughout the opening/closing range of motion of the jaw members.

Moreover, although some teleoperated surgical systems include sensors that are configured to detect a position of the gripping jaw members, and to control or restrict deployment of the cutting element while the jaw members are open beyond a specified threshold, the complementary retaining feature provided on at least one jaw member prevents the cutting element from slipping out of its tracks or the drive element of the cutting element from bending and changing an angle of the cutting element. Further, for existing systems that are not configured with such capabilities, the disclosed retention features mitigate the risk of the cutting element slipping out of alignment. In exemplary embodiments wherein the gripping surfaces of the jaw members also are configured to deliver energy to perform electrosurgical procedures, the tissue may be gripped by the jaw members prior to being fused through the application of electrosurgical energy. In other embodiments, the cutting element can be used to perform cold cutting in which tissue gripped between the gripping surfaces is subjected to cutting without any energy being delivered prior to the cutting procedure.

With reference now to FIG. 1, a perspective view of a minimally invasive surgical instrument 100 is illustrated. The directions "proximal" and "distal" are used herein to define the directions as shown in FIG. 1, with distal generally being in a direction further along a kinematic arm or closest to the surgical work site in the intended operational use of the instrument 100, for example, in use for performing surgical procedures. As shown in FIG. 1, the instrument 100 generally includes a force/torque/position drive transmission mechanism 101, an instrument shaft 102 mounted to the transmission mechanism 101, an end effector 103 disposed at the distal end of the instrument 100, and an optional articulation wrist 104 disposed at a distal end of the shaft 102 to support the end effector 103 on the shaft 102. End effector 103 can be one of a variety of types as described above, and may comprise various configurations. In one exemplary embodiment, end effector 103 may be a gripping end effector comprising gripping jaw members with electrodes configured to perform electrosurgical procedures, such as sealing and cutting, on a material such as, for instance, tissue. When configured for electrosurgical applications, end effector 103 may operate in a monopolar or bipolar mode to deliver electrical flux for sealing, while further using mechanical actuation for deploying a cutting element. End effector 103 can also operate in harmonic, laser, and ultrasonic modes to deliver types of energy other than electrical or mechanical energy. An exemplary embodiment of a gripping end effector is further described with reference to FIGS. 3-4.

Figure 2:
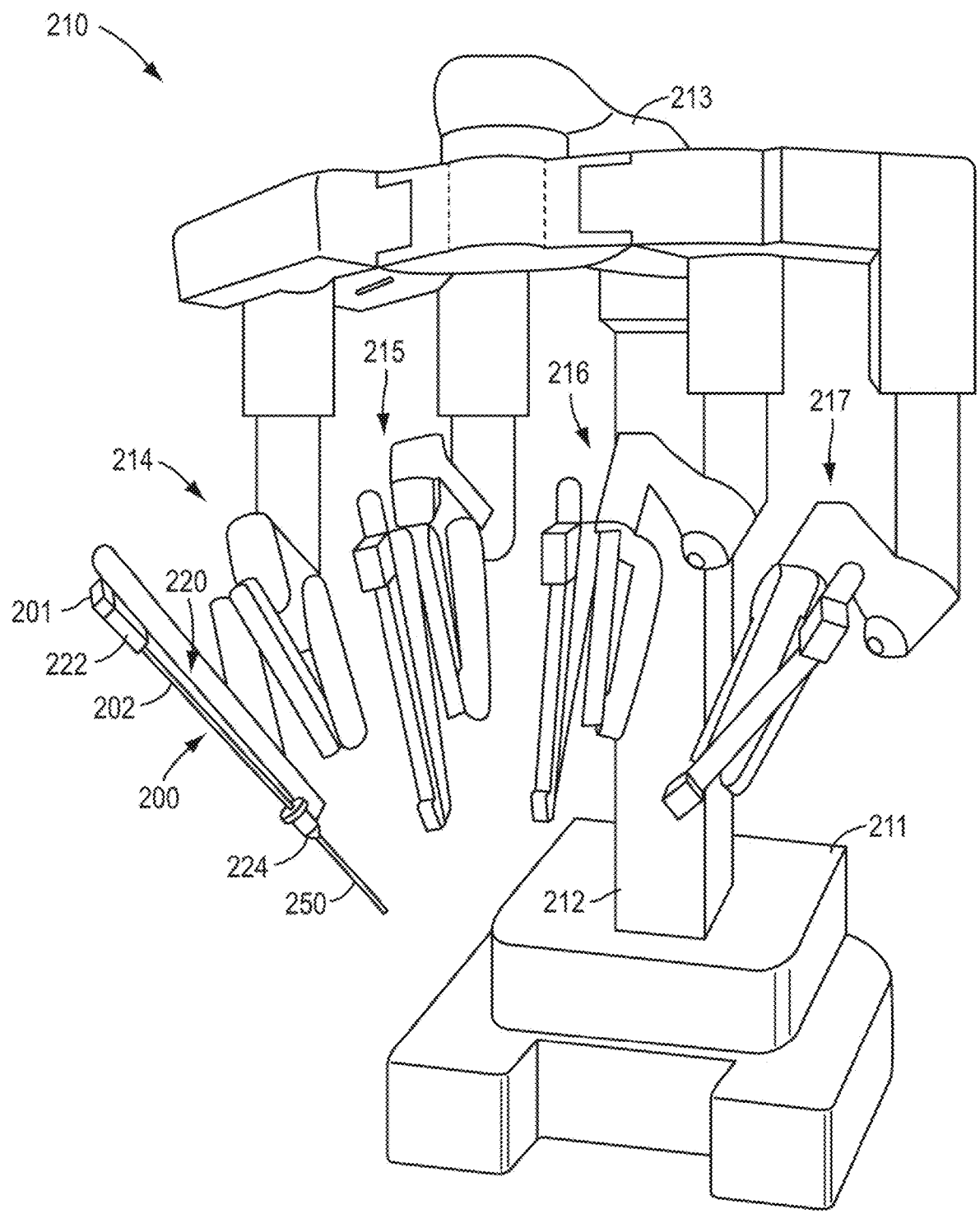
FIG. 2 shows a perspective view of an exemplary embodiment of a patient side cart of a teleoperated, computer-assisted surgical system.

As discussed above, in accordance with various exemplary embodiments, surgical instruments of the present disclosure are configured for use in teleoperated, computer-assisted surgical systems (sometimes referred to as robotic surgical systems). Referring now to FIG. 2, an exemplary embodiment of a patient side cart 210 of a teleoperated, computer-assisted surgical system, to which surgical instruments are configured to be mounted for use, is shown. Such a surgical system may further include a surgeon console (not shown) for receiving input from a user to control instruments of patient side cart 210, as well as an auxiliary control/vision cart (not shown), as described in, for example, U.S. Pub. No. US 2013/0325033, entitled "Multi-Port Surgical Robotic System Architecture" and published on Dec. 5, 2013, and U.S. Pub. No. US 2013/0325031, entitled "Redundant Axis and Degree of Freedom for Hardware-Constrained Remote Center Robotic Manipulator" and published on Dec. 5, 2013, each of which is hereby incorporated by reference in its entirety. Non-limiting, exemplary embodiments of teleoperated surgical systems with which the principles of the present disclosure may be utilized include the da Vinci® Si Surgical System, Single Site da Vinci® Surgical System, and da Vinci® Xi Surgical System, available from Intuitive Surgical, Inc. of Sunnyvale, Calif. However, persons having ordinary skill in the art will appreciate that the present disclosure can be applied to a variety of other teleoperated, computer-assisted surgical systems as well as other automated or manual (hand-held) laparoscopic surgical systems.

Patient side cart 210 includes a base 211, a main column 212, and a main boom 213 connected to main column 212. Patient side cart 210 also includes a plurality of jointed set-up arms 214, 215, 216, 217, which are each connected to main boom 213. In other exemplary embodiments, any number of manipulator arms is contemplated as within the scope of the subject disclosure. Arms 214, 215, 216, 217 each include an instrument mount portion 220 to which an instrument may be mounted, such as instrument 200, which is illustrated as being attached to arm 210. Arms 214, 215, 216, 217 further include manipulator portions that can be manipulated during a surgical procedure according to commands provided by a user at the surgeon console. In an exemplary embodiment, signal(s) or input(s) transmitted from a surgeon console (not shown) are transmitted to a control/vision cart (not shown), which interprets the input(s) and generate command(s) or output(s) to be transmitted to the patient side cart 210 to cause manipulation of an instrument 200 and/or portions of arm 214 to which the instrument 200 is coupled. Those having ordinary skill in the art would understand that the processor/controller functionality need not be included in an auxiliary/vision cart separate from the patient side cart and surgeon console, but rather could be on a different piece of equipment, on the surgeon console or patient side cart, or distributed between those components.

Instrument mount portion 220 comprises an actuation interface assembly 222 and a cannula mount 224, with a force transmission mechanism 201 of instrument 200 connecting with the actuation interface assembly 222. Cannula mount 224 is configured to hold a cannula 250 through which shaft 202 of instrument 200 may extend to a surgery site during a surgical procedure. Actuation interface assembly 222 contains a variety of drive and other mechanisms that are controlled to respond to input commands at the surgeon console and transmit forces to the force transmission mechanism 201 to actuate instrument 200, as those skilled in the art are familiar with.

Although the exemplary embodiment of FIG. 2 shows an instrument 200 attached to only arm 214 for ease of viewing, an instrument may be attached to any and each of arms 214, 215, 216, 217. An instrument 200 may be a surgical instrument with an end effector, such as instrument 100 as discussed above with reference to FIG. 1. A surgical instrument with an end effector may be attached to and used with any of arms 214, 215, 216, 217. However, the embodiments described herein are not limited to the exemplary embodiment of FIG. 2, and various other teleoperated, computer-assisted surgical system configurations may be used with the exemplary embodiments described herein.

Referring again to FIG. 1, the transmission mechanism 101 transmits received actuation inputs, for example, from a patient side cart (such as 210) in computer-assisted surgical systems or manually, to resulting torques and forces to effect movement of the instrument shaft 102, optional wrist 104, end effector 103, and/or associated components, to accomplish various motions, potentially resulting in a multiple-degrees-of-freedom (multi-DOF) actuation of the surgical instrument. For example, the transmission mechanism 101 can be controlled via inputs (e.g., torque inputs) to roll shaft 102, and consequently end effector 103 (roll DOF), open and close jaw members of the end effector 103 (grip or clamp DOF), and articulate wrist 104 (articulation DOF), among others. In various exemplary embodiments, the wrist 104 can be configured for one-DOF or two-DOF articulation in orthogonal directions to provide "pitch" and/or "yaw" movement of end effector 3 (yaw being arbitrarily defined as being the plane of motion of the end effector jaw members, pitch being orthogonal to yaw). In addition, a cutting element can be independently controlled in translation DOF for movement relative to the end effector substantially along a longitudinal direction of the end effector jaws, even when the wrist is articulated in pitch and/or yaw relative to a longitudinal axis of the instrument shaft, and/or when the instrument shaft and end effector are rolled (i.e., rotated about the longitudinal axis of the shaft).

In embodiments wherein the instrument is an electrosurgical instrument, the transmission mechanism 101 also can accommodate electrical conductors (not shown in FIG. 1) to receive electrical energy via connector 106 that is electrically coupled to an electrical flux generation source such as, for example, an electrosurgical supply unit (ESU). The ESU may be remotely controlled by a surgeon via a surgeon console, as discussed above. Electrical conductors include wires and other types of conductors (for example, ultrasonic) for actuating and for delivering flux (for example, electrical, thermal, or ultrasonic energy) from one or more ESU's to end effector 103, whereupon the flux may be used to perform electrosurgical procedures, such as fuse, cauterize, or cut tissue and/or tissue-like materials. The conductors can be routed from the transmission mechanism 101, down the instrument shaft 102 to the end effector 103.

Additional details regarding exemplary, but non-limiting, embodiments of electrosurgical instruments that include a transmission mechanism and a jawed end effector with opposing electrode assemblies configured for performing fusing and cauterizing (e.g., vessel sealing) in combination with a translating cutting element are disclosed in U.S. Pat. No. 9,055,961 B2, and being titled "FUSING AND CUTTING SURGICAL INSTRUMENT AND RELATED METHODS," and issued Jun. 16, 2015, which is hereby incorporated by reference herein in its entirety.

Figure 3A:
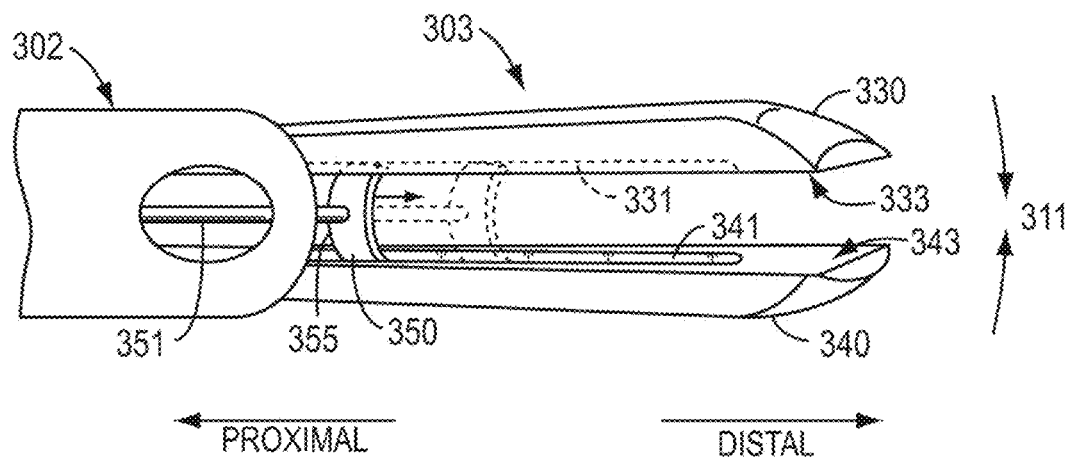
FIGS. 3A and 3B show magnified perspective views of a distal end portion of an exemplary embodiment of a surgical instrument with a gripping and cutting end effector in closed and open positions, respectively.
Figure 3B:
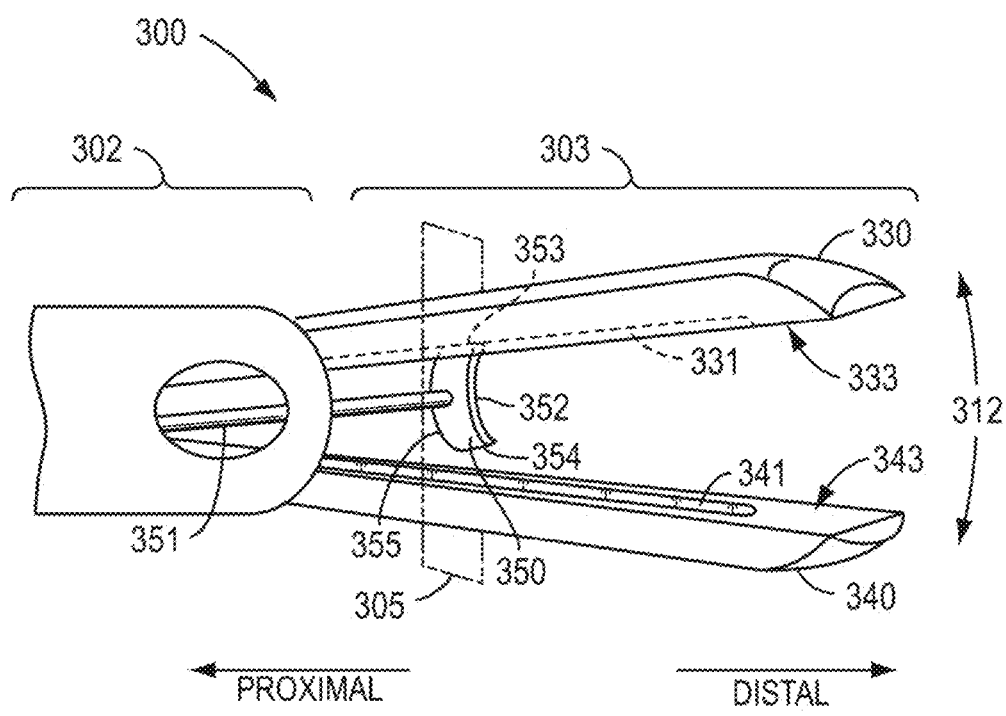

FIGS. 3A and 3B show magnified perspective views of a distal end portion of an exemplary embodiment of a surgical instrument 300 with a gripping and cutting end effector 303 in closed and open positions, respectively. In this embodiment, gripping end effector 303 comprises a pair of opposing jaw members including an upper jaw member 330, lower jaw member 340, and cutting element 350. For the purposes of this embodiment, the words "upper" and "lower" describe relative positions with respect to the orientation shown in FIG. 3; those having ordinary skill in the art would appreciate, however, that the relative positions of the jaw members can be reversed, such as, for example, when the instrument shaft and end effector are subjected to a roll motion. Upper jaw member 330 and lower jaw member 340 may be closed as depicted in FIG. 3A (i.e., one or each jaw member being moved toward the other or each other in directions 311 respectively) and opened as depicted in FIG. 3B (i.e., one or each jaw member being moved away from the other or each other in direction 312 respectively), via mechanical actuation elements routed through surgical instrument 300, such as from a transmission housing (not shown) along the instrument shaft 302 and to end effector 303. Each jaw member 330, 340 may be independently actuated such that each jaw member can respectively move in directions 311, 312 independently of the other jaw member.

Further, over a gripping range of motion from a closed position (i.e., the limit of closure defined between the jaws) to a position intermediate the full range of motion of the jaw members, jaw members 330 and 340 can be used to grip a material, such as tissue, between gripping surfaces 333, 343 of jaw members 330 and 340 respectively. Cross-sections along direction 305 of a gripping end effector gripping a material are further described with respect to FIGS. 4A and 4B. For the purposes of this disclosure, "gripping surfaces" are any surfaces of gripping end-effectors that grip material, such as tissue, and that optionally deliver energy to perform electrosurgical procedures. The gripping surfaces may comprise opposite-facing surfaces of each jaw member. For example, a lower surface 333 of upper jaw member 330 and upper surface 343 of lower jaw member 340 collectively comprise gripping surfaces. The tissue may be gripped using the jaw members 330 and 340, and cut using cutting element 350.

In this embodiment, cutting element 350 is generally planar in shape, with its main planar faces extending in a proximal-distal direction, (i.e., along a length of jaw members 330, 340). For example, cutting element 350 comprises edges surrounding the planar faces including opposite edges to be received in respective grooves 331 and 341 provided on surfaces 333, 343. To perform the cutting procedure, cutting element 350 is deployed (as depicted in FIG. 3A) from a proximal-most position (i.e., "garaged" position) to a distal-most position, by being translated along a length of grooves 331 and 341 in a proximal-distal direction. Cutting element 350 is translated by cutting element drive component 351 coupled to proximal edge 355 of cutting element 350. Distal edge 352 is sharpened to enable cutting of the material gripped between the gripping surfaces 333, 343 as cutting element 350 is deployed. At least for a teleoperated surgical instrument, the translation can occur via, for instance, a controller and software that controls the operation to drive cutting element drive component 351 through drives in a transmission housing (not shown) at a proximal end of the shaft of the instrument.

As shown in the exemplary embodiment of at least FIGS. 3A and 3B, cutting element drive component 351 can comprise a cable having a distal end that is welded to the proximal end of cutting element 350. To avoid sharp edges and/or blunt surfaces where cutting element 350 attaches to cutting element drive component 351, cutting element 350 and cutting element drive component 351 may be blend welded together to provide a smooth interface between the two components. Providing a relatively smooth interface between the two components can reduce the risk of having cutting element 350 become stuck on material during a cutting procedure. Cutting element drive component 351 is attached at a proximal end to a transmission mechanism (not shown), which is configured to provide a linear (push/pull) motive force to cutting element drive component 351 and allow roll multiple degrees of freedom as described above. The cable structure of cutting element drive component 351 is sufficiently flexible so as to withstand bending in various directions about its longitudinal axis, while also providing sufficient compressive and tensile strength to withstand and transmit the push/pull actuation forces from the transmission mechanism to translate cutting element 350, including through the material in order to effect cutting. For example, end effector 303 may be coupled to a wrist provided at the distal end of instrument shaft 302, with the wrist being configured to articulate in multiple degrees of freedom. Cutting element drive component 351 can be centrally routed through shaft 302 including the wrist, and can be flexible in multiple degrees of freedom about a longitudinal axis. The central routing of cutting element drive component 351 permits surgical instrument 300 to have a relatively compact design, while also providing centering of cutting element 350 relative to end effector 303 during the cutting procedure. Further, central routing of cutting element drive component 351 can reduce friction that acts on cutting element drive component 351 as it is articulated and/or rolled when translating cutting element 350. In this way, the force required to deploy cutting element 350 can be reduced in comparison with a configuration in which cutting element drive component 351 is routed toward an outer periphery of the instrument as opposed to centrally. Further, central routing of cutting element drive component 351 can result in substantially no change of length during articulation of end effector 303, allowing cutting element 350 to remain in a garaged position during articulation.

In an alternative embodiment (not shown), rather than a cable structure, cutting element drive component 351 can include a superelastic flexible wire having a high tensile and compressive strength, such as, for example, a nitinol wire. The flexibility of cutting element drive component 351 enables flexion as the jaw members 330, 340 are moved between open and closed positions, allowing reduced friction and easier tracking of the cutting element 350 in groove 331. Other exemplary embodiments of drive components that are contemplated as within the scope of the present invention that can be used in lieu of a flexible cable or wire structure, include a planar sheet metal component that can be integral with the cutting element by providing the distal end of such a member with a sharpened cutting surface. The use of such a structure may be combined, for example, with a non-wristed instrument or an instrument having a wrist that articulates in one degree of freedom.

Grooves 331 and 341 are configured as tracks for maintaining the movement of cutting element 350 in the proximal-distal (and vice-versa) direction as the cutting element is translated. In other words, grooves 331 and 341 guide and keep cutting element 350 aligned as it travels along the length of jaw members 330, 340. Further, and as described herein, a retaining feature (not shown) can be coupled to cutting element 350, and received by a slot within groove 331. Like groove 331, the slot runs along a portion of the length of gripping surface 333 of jaw member 330, and retains the retaining feature when jaw members 330, 340 are in an open position, as depicted in FIG. 3A. For example, in the open position, one or both of jaw members 330, 340 may be open to a degree such that at the location of cutting element 350, a distance between grooves 331, 341 provided on gripping surfaces 333, 343 is greater than the height h of cutting element 350, such that an opposite edge of cutting element 350 is outside groove 341. Groove 341 runs along a portion of the length of gripping surface of jaw member 340 and, in a closed position of the jaw members 330, 340, is adapted to receive the opposite edge of cutting element 350. Thus, while groove 331 includes a slot configured to house the retaining feature, groove 341 can be configured to house a lower edge 354 of cutting element 350 while jaw members 330 and 340 are in a closed position (as shown in FIG. 3B), while releasing the cutting element 350 when the jaw members 330 and 340 open away from each other. The length of grooves 331 and 341 can be approximately 70% of the overall length of the jaw members from where they are pivotally connected together. For example, in various exemplary embodiments, each jaw member may be between ⅝" and 1" long from end to end or, for example, ⅞" in length. Each groove 331, 341 have a length ranging from 0.4" to a maximum of the length of the jaw itself, e.g., 1". In the distal-most position, the distal cutting edge of cutting element 350 can be positioned at a distal end of grooves 331, 341 respectively provided on the gripping surfaces of jaw members 330, 340.

Figure 4A:
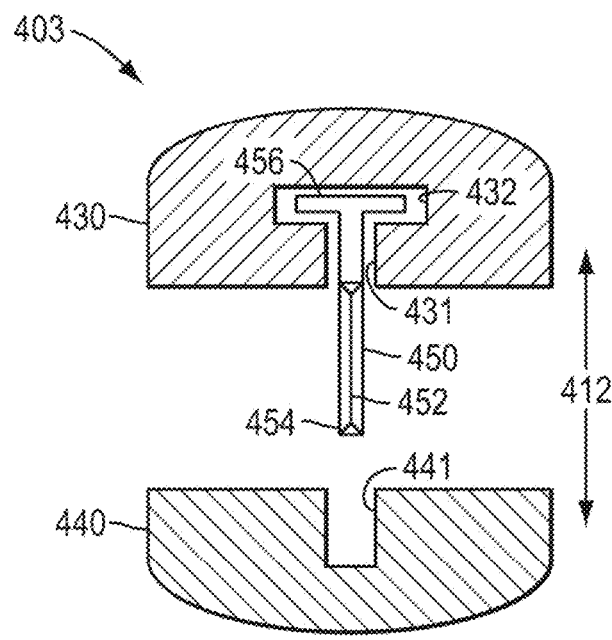
FIGS. 4A and 4B show cross-section views of an exemplary embodiment of a gripping end effector in open and closed positions, respectively.
Figure 4B:
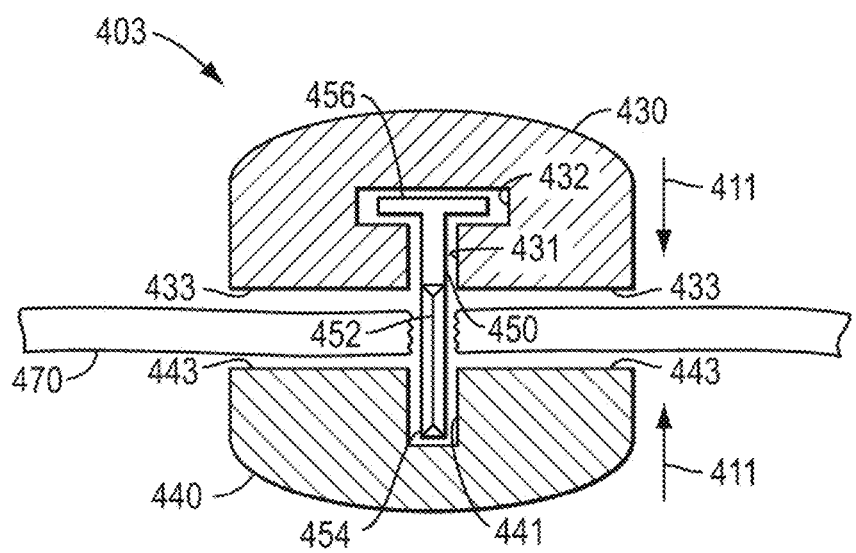

FIGS. 4A and 4B show cross-section (i.e., transverse to the lengthwise direction of the jaws) views of an exemplary embodiment of a gripping end effector 403 in open and closed positions, respectively. Gripping end effector 403 comprises a pair of jaw members 430, 440, and a cutting element 450. The cutaway view depicts a cross-section along cutaway 305 of exemplary gripping end effector 303 depicted in FIG. 3. End effector 403 comprises a pair of jaw members 430 and 440 that are configured to grip a material 470 between gripping surfaces 433, 443 of jaw members 430, 440, and a cutting element 450 configured to cut material 470 as it is gripped between the gripping surfaces. Coupled to cutting element 450 is a retaining feature in the form of a flange 456 that extends laterally at an angle relative to the plane of cutting element 450. Retaining flange 456 can be received within a complementary negative retaining feature, such as slot 432 opening from groove 431 of upper jaw member 430. Retaining flange 456 presents a stop for preventing cutting element 450 from being removed from groove 431 and slot 432. Consequently, slot 432 holds cutting element 450 in position as the jaw members are in an open position along direction 412, as depicted in FIG. 4A. Further, like groove 431, slot 432 runs along a portion of the length of jaw member 430 in the proximal-distal direction, and is configured to house retaining flange 456 as cutting element 450 is translated along the length of end effector 403, thereby forming a track for cutting element 450 along with groove 431. A second groove 441 runs along a portion of the length of gripping surface 443 of lower jaw member 440, and is configured to house a lower portion 454 of cutting element 450 while jaw members 430 and 440 are moved along direction 411 into a closed position, as depicted in FIG. 4B. To perform the cutting procedure, cutting element 450 is translated in the proximal-distal direction by a cutting element drive component (not shown) coupled to the proximal edge of cutting element 450, as previously described. Sharp edge 452 is provided on the distal edge of cutting element 450 to enable cutting of material 470 gripped between the gripping surfaces of jaw members 430, 440. Thus, second groove 441 functions as a track for lower edge 454 of cutting element 450.

Figure 5:
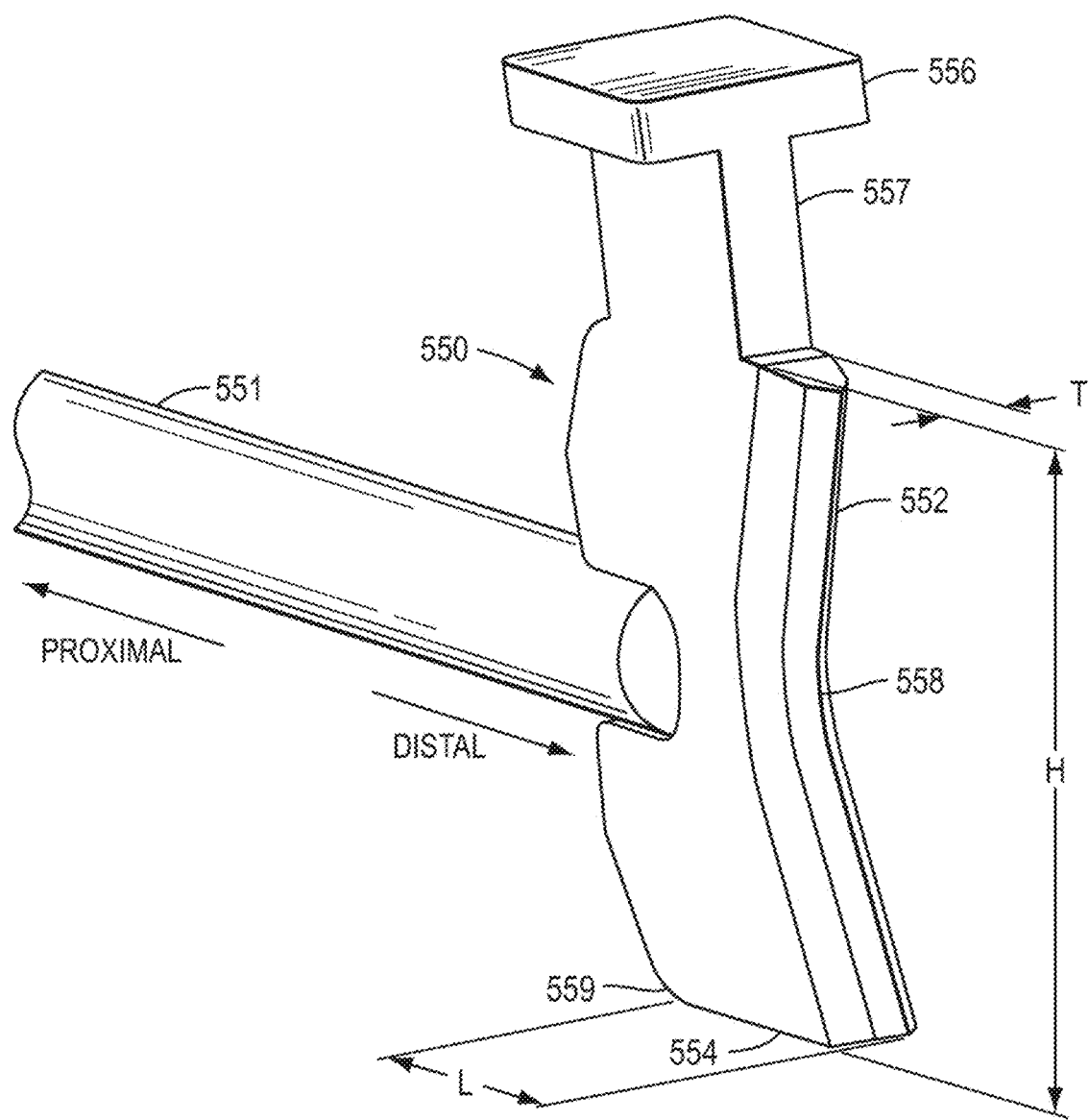
FIG. 5 shows a detailed perspective view of an exemplary embodiment of a cutting element coupled to a cutting element drive component and a retaining flange.

FIG. 5 is a detailed perspective view of an exemplary embodiment of a cutting element 550 coupled to a cutting element drive component 551 and a retaining flange 556. Cutting element 550 is generally planar in shape, as described above. Retaining flange 556 is oriented at perpendicular angle to the plane of cutting element 550, and can be configured to be received and retained in a corresponding slot of a jaw member (e.g., such as the upper jaw member in the orientation of above-described embodiments). In other embodiments, retaining flange 556 may be oriented at angles other than perpendicular to the plane of the cutting element 550, so long as there remains a transverse component that enables retention of cutting element 550 in a slot of a jaw member as the jaw members open to an amount sufficient such that although opposing edge 554 of cutting element 550 would be removed from a corresponding groove of a jaw member, cutting element 550 remains aligned. In other embodiments, retaining flange 556 can be any shape, so long as it restricts the motion of cutting element 550 in any direction other than the direction of translation, thereby retaining cutting element 550 within a track of a jaw member regardless of the degree to which the jaws are opened with their gripping surfaces and spaced.

Retaining flange 556 can include a member 557 for coupling to an upper portion of cutting element 550. Member 557 can generally be shaped in the plane of cutting element 550, and transverse to the retaining flange 556, such that the flange 556 and member 557 form approximately a T-shape. Cutting element 550, member 557, and retaining flange 556 may be manufactured from a single piece of material. For example, cutting element 550, member 557, and retaining flange 556 may be machined or metal injection molded. In other embodiments, such as the alternative orientations of retaining flange 556 described above, cutting element 550 may be stamped from a single sheet of material, and a portion of cutting element 550 may be bent away from the plane of the sheet and formed into a retaining flange. In other embodiments, the retaining flange may be machined or manufactured separately from the cutting element, and attached to the cutting element using spot welding, resistance welding, or other types of fasteners or adhesive.

Further, as described above, a distal edge 552 of cutting element 550 may be sharpened for cutting material as cutting element 550 is deployed in the distal direction. In one exemplary embodiment, sharp edge 552 may be angled inwardly (e.g., concave), such that the material being cut is drawn closer to the middle 558 of sharp edge 552 as cutting element 550 is deployed or translated in the distal direction. In other words, a concave "V" shape 558 in cutting edge 552 can assist in pulling tissue into the cutting surface. However, such configuration is non-limiting and exemplary only, and in other configurations the sharp edge 552 may have a straight, angled, or curved (including convex), or combinations thereof, cutting surface. Moreover, the distal edge of member 557 connecting to retaining flange 556 may also be sharpened, thereby integrating with cutting edge 552 and increasing the length of the edge usable to cut material, as further described with respect to the exemplary embodiment of FIGS. 9A-9C.

In an exemplary embodiment, the proximal end of cutting element 550 may have rounded corners such as corner 559 leading to opposing edge 554 and main lateral planar surfaces, so as to minimize the risk of cutting element 550 getting stuck when retracted (i.e., translated in the proximal direction) after completion of a cutting procedure. In various exemplary embodiments, cutting element 550 is made of stainless steel (e.g., 716 stainless steel) and has a double grind cutting edge 552. Cutting element 550 can be secured to cutting element drive component 551 by various mechanisms, including, for example, welding. In various exemplary embodiments, cutting element 550 has a height H ranging from about 0.08 in. to about 0.15 in., for example about 0.10 in., a length L (in the proximal-distal direction) ranging from about 0.10 in. to about 0.13 in., for example, about 0.115 in, and a thickness T ranging from about 0.005 in. to 0.015 in.

Figure 6A:
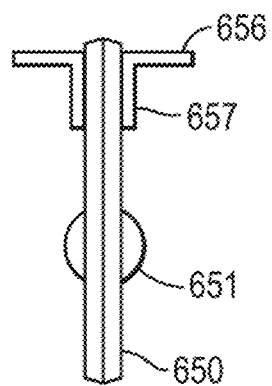
FIGS. 6A and 6B respectively show front and perspective views of an exemplary embodiment of a cutting element and a separate retaining flange attached to the cutting element with an extension component that extends generally parallel to the plane of the cutting element.
Figure 6B:
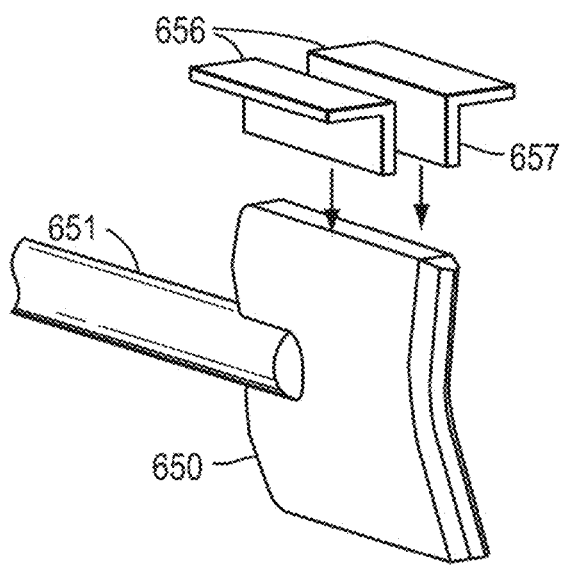

As described herein, in some embodiments, the retaining flange may be machined or manufactured separately from the cutting element, and attached to the cutting element using spot welding, resistance welding, or other types of fasteners or adhesive. FIGS. 6A-6B respectively show front and perspective views of an exemplary embodiment of a cutting element 650 and a separate retaining flange 656 attached to cutting element 650 with an extension component 657 that extends generally parallel to and along the lateral planar faces of the cutting element 650. Extension component 657 enables securing retaining flanges 656 on the opposite lateral planar faces of cutting element 650. Cutting element 650 is generally planar in shape, and is depicted in a vertical orientation such that it extends between an upper jaw member and a lower jaw member (not shown). Retaining flange 656 is, therefore, oriented at an angle to the plane of cutting element 650, such that it is retained in a corresponding slot of the upper jaw member and presents a stop for preventing cutting element 650 from being removed from the groove/slot in the upper jaw member. Retaining flange 656 and extension component 657 may be machined or manufactured from a single piece of material separately from cutting element 650, and attached to cutting element 650 using spot welding, resistance welding, or other types of fasteners or adhesive. Separately manufacturing these components enables cutting element 650 to be manufactured from a hard material that holds a cutting edge well, while retaining flanges 656 may be manufactured from a different material, for example, a material that is bendable.

Figure 8:
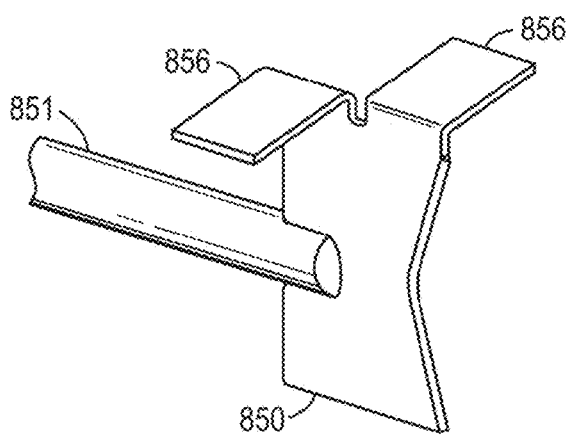
FIG. 8 shows a perspective view of an exemplary embodiment of a cutting element stamped from a single sheet of material with a portion of the cutting element bent away from the plane of the sheet to form a retaining flange.

However, in other embodiments, it may be more economical or convenient to manufacture the cutting element and retaining flange from a single piece of material. FIG. 8 shows a perspective view of an exemplary embodiment of a cutting element 850 stamped from a single sheet of material, with portions of the cutting element bent away from the plane of the single sheet of material to form retaining flanges 856. Cutting element 850 is generally planar in shape, and is depicted in a vertical orientation such that it extends between an upper jaw member and a lower jaw member (not shown). Retaining flanges 856 are, therefore, oriented at an angle to the plane of cutting element 850, such that they are retained in a corresponding slot of the upper jaw member, and present a stop for preventing cutting element 850 from being removed from the groove/slot in the upper jaw member.

Figure 7A:
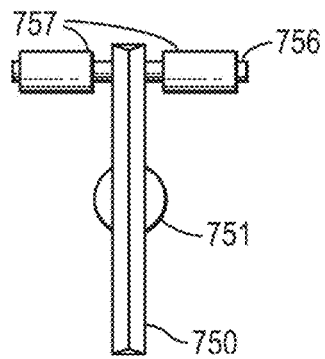
FIGS. 7A, 7B, and 7C respectively show front, perspective, and side views of an exemplary embodiment of a cutting element with a retaining pin extending laterally outwardly from the planar surfaces of the cutting element in a direction generally transverse to the lengthwise direction of the jaw members.
Figure 7B:
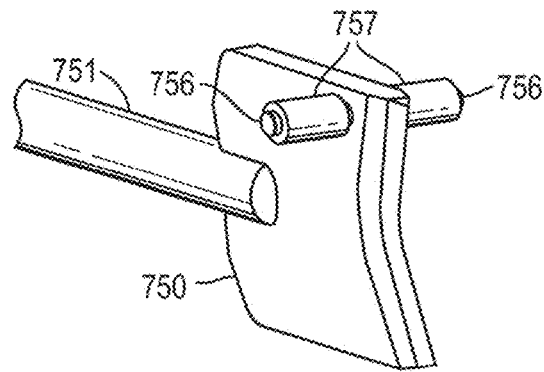
Figure 7C:
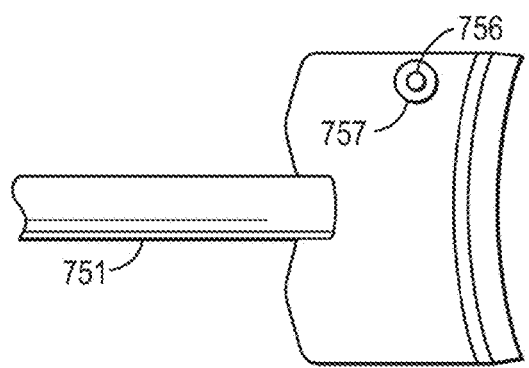

Generally, a retaining feature can be any shape suitable for restricting the motion of the cutting element in any direction other than the direction of translation, thereby retaining the cutting element within a track of a jaw member as the cutting element is deployed. In another exemplary embodiment, the retaining feature may be configured as a pin. FIGS. 7A, 7B, and 7C respectively show front, perspective, and side views of an exemplary embodiment of a cutting element with a retaining pin 756 extending laterally outwardly from the planar surfaces of cutting element 750 in a direction generally transverse to the lengthwise direction of the jaw members. Similar to the retaining flanges described above with respect to various embodiments, retaining pin 756 extends laterally outwardly (e.g., horizontally in the orientation of the figures) relative to the plane of the cutting element 750. In other words, pin 756 intersects the plane of the cutting element 750 at an angle, such as for example perpendicular, to the plane of the cutting element 750. In other embodiments, a retaining pin 756 may be oriented at other angles than the perpendicular orientation depicted herein, so long as there remains a transverse component relative to the plane of cutting element 750 that enables retention of cutting element 750 in a slot of a jaw member in manner similar to the retention flanges described above.

In some embodiments, retaining pin 756 can be configured to roll along the complementary negative retaining feature in the jaw member (e.g., slot) in which the pin is received as cutting element 750 is deployed and retracted. A rolling component or sleeved roller 757 comprising a concentric cylinder or ring may be provided over each side of retaining pin 756 to enable frictionless rolling along the length of a retaining slot of a jaw member. In other embodiments, a sleeve or coating may be provided over the surfaces of retaining pin 756 to reduce friction as against the surfaces of the jaw member defining the complementary retaining feature. Moreover, for these and other embodiments herein, surfaces of a retaining flange or pin and corresponding groove or slot may be electropolished, such that they are smooth and minimize friction during deployment and retraction of the cutting element. Similarly, any sharp corners or edges can be treated such that they are rounded to reduce friction.

Figure 9A:
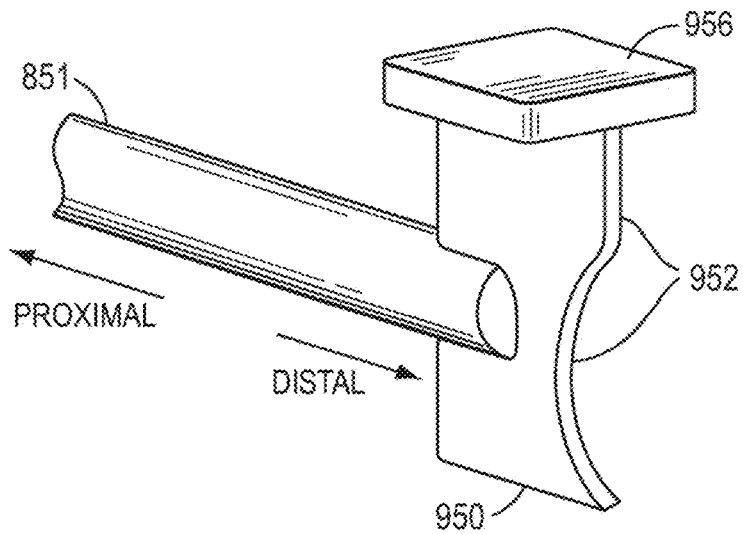
FIGS. 9A, 9B, and 9C respectively show perspective, side, and front, views of an exemplary embodiment of a cutting element comprising a sharp edge extending to the retaining flange.
Figure 9B:
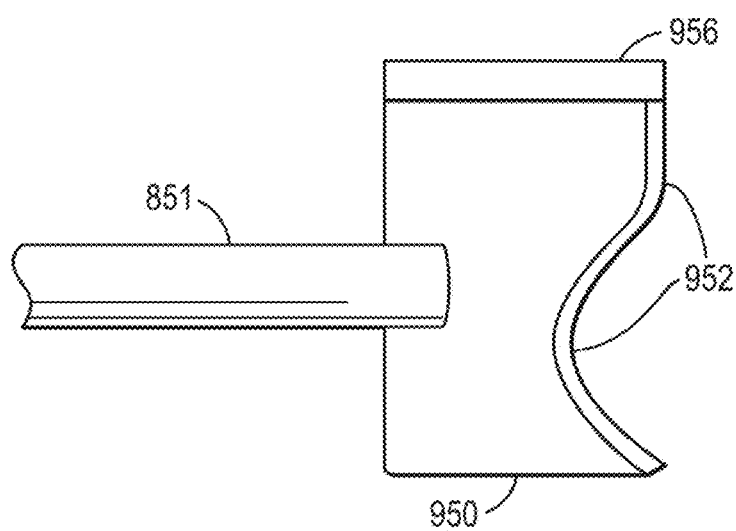
Figure 9C:
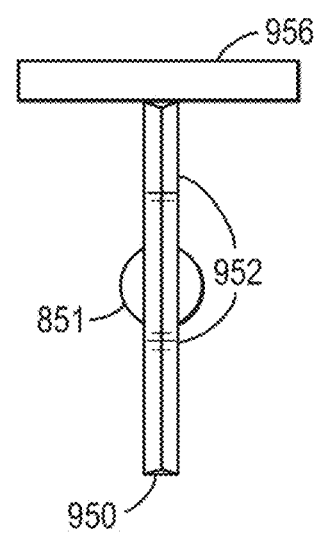

FIGS. 9A, 9B, and 9C respectively show perspective, side, and front views of an exemplary embodiment of a cutting element 950 comprising a sharp edge 952 extending to the retaining flange 956, thereby increasing the length of the edge usable to cut material. Similar to the embodiment of FIG. 5, cutting element 950 is generally planar in shape, with retaining flange 956 oriented at an angle perpendicular to the plane of cutting element 950. Retaining flange is configured to be received and retained in a corresponding slot of a jaw member (e.g., such as the upper jaw member in the orientation of above-described embodiments). Cutting element 950 and retaining flange 956 may be manufactured from a single piece of material that is machined or metal injection molded, or retaining flange 956 may be machined or manufactured separately from cutting element 950, and attached to cutting element 950 using spot welding, resistance welding, or other types of fasteners or adhesive.

Figure 10A:
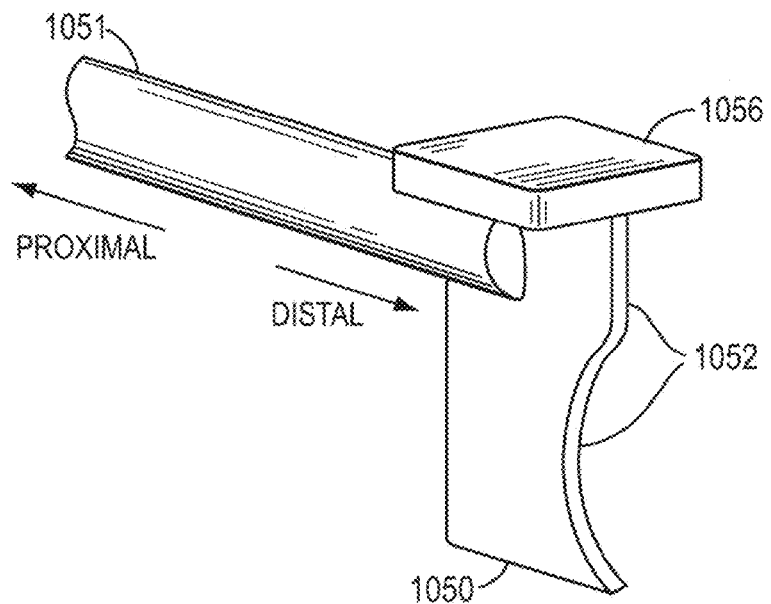
FIGS. 10A, 10B, and 10C respectively show perspective, side, and front views of an exemplary embodiment of a cutting element drive component coupled to a portion of the cutting element that is proximate a groove of a jaw member.
Figure 10B:
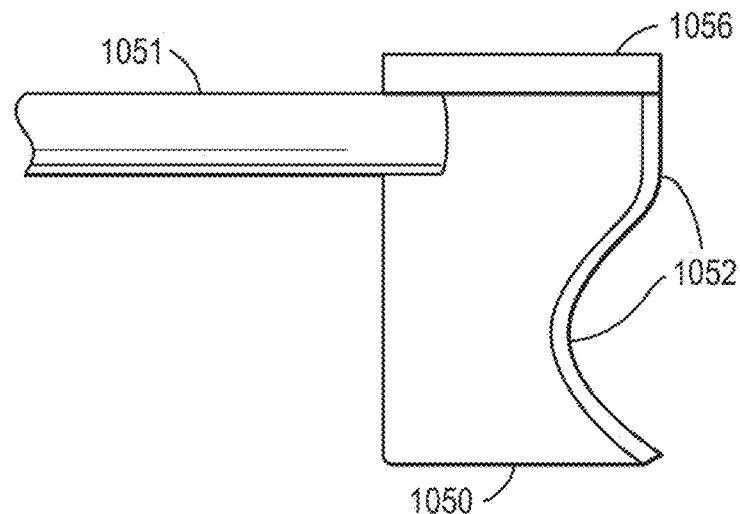
Figure 10C:
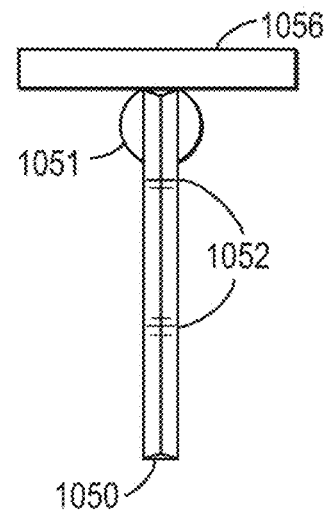

FIGS. 10A, 10B, and 10C respectively show perspective, side, and front views of an exemplary embodiment of a cutting element drive component 1051 coupled to a portion of cutting element 1050 that is proximate a groove of a jaw member. Similar to the embodiment of FIGS. 9A-9C, cutting element 1050 is generally planar in shape, with retaining flange 1056 oriented at an angle perpendicular to the plane of cutting element 1050 and configured to be received and retained in a corresponding slot of a jaw member (e.g., such as the upper jaw member in the orientation of above-described embodiments). In this embodiment, cutting element drive component 1051 is vertically shifted to a position closer to retaining flange 1056. Consequently, cutting element drive component 1051 is closer to or may be enclosed within a groove of an opposing surface of a jaw member configured to house retaining flange 1056. This proximity or enclosure by a groove hinders excess movement or flex in cutting element drive component 1051 as cutting element 1050 is translated, thereby preventing tipping or binding of cutting element drive component 1051 in the groove.

Figure 11A:
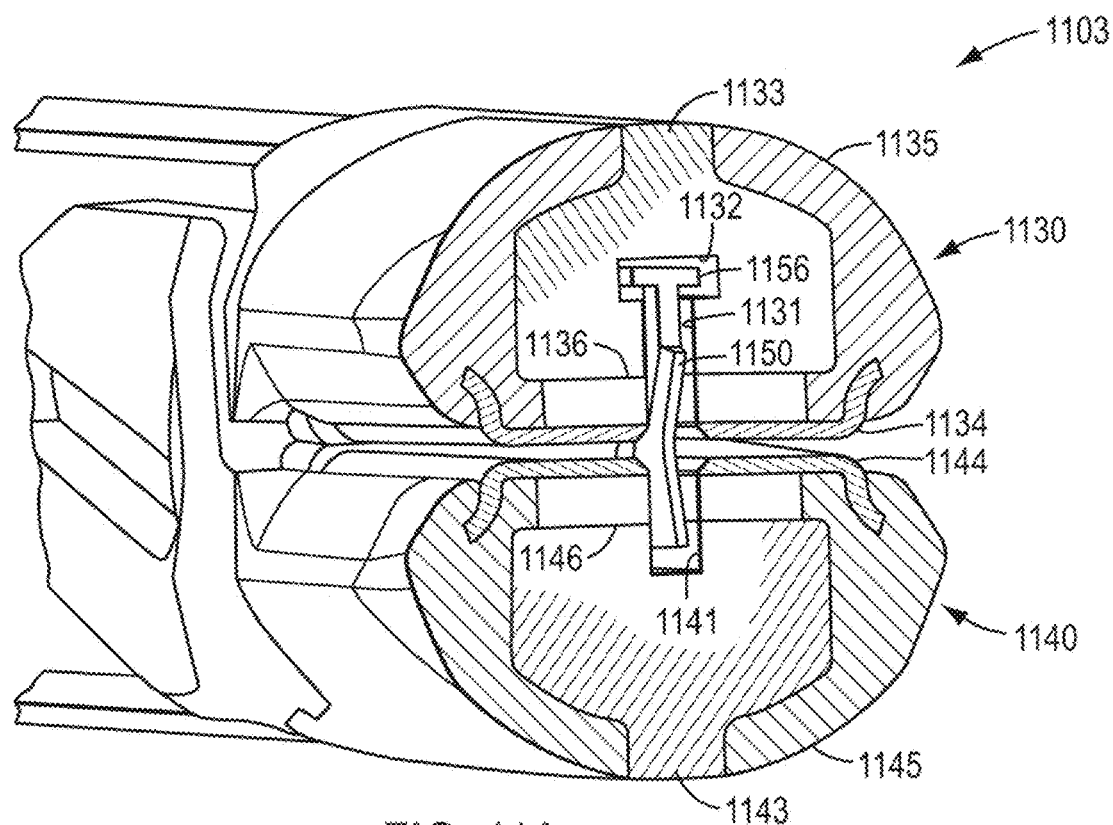
FIGS. 11A and 11B show cutaway perspective views of an exemplary embodiment of an electrosurgical end effector comprising a pair of gripping jaw members and a cutting element in a retracted position and a deployed position, respectively.
Figure 11B:
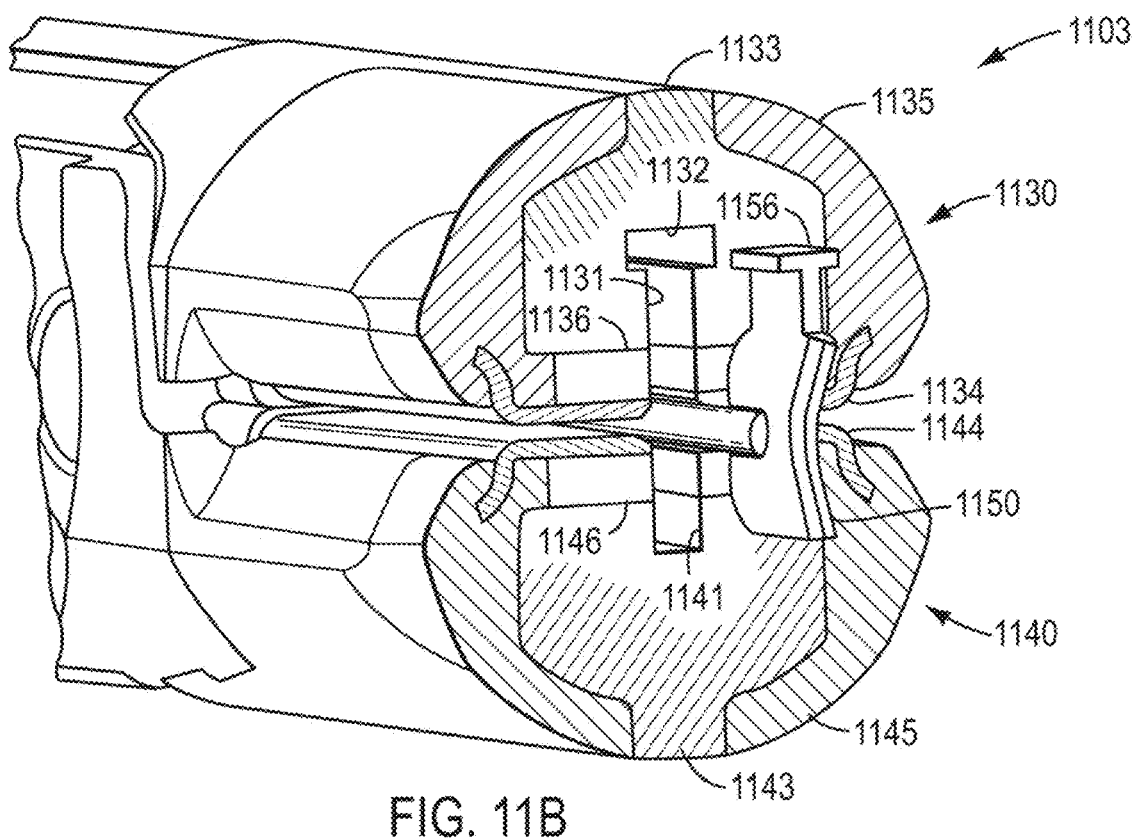

Optionally, jaw members of an end effector may further be provided with electrode surfaces configured to deliver electrosurgical energy, for example to fuse tissue, with the cutting element being used to cut the fused tissue. FIGS. 11A-11B are cutaway views of an exemplary embodiment of an electrosurgical end effector comprising a pair of gripping jaw members 1130, 1140, and a cutting element 1150 in a retracted position (FIG. 11A) and a deployed position (FIG. 11B). Upper jaw member 1130 and lower jaw member 1140 may be opened, i.e. moved away from each other, and closed, i.e. moved toward each other. In a closed position, jaw members 1130 and 1140 can be used to grip a material, such as tissue, between gripping surfaces of jaw members 1130 and 1140. As further described herein, cutting element 1150 is deployed to cut the material gripped between the gripping surfaces.

Each jaw member 1130, 1140 respectively includes a metal body portion 1133, 1143 that provides structural rigidity to end effector 1103. Grooves 1131 and 1141 for retaining upper and lower portions of cutting element 1150 may be provided within metal body portions 1133, 1143. Generally, grooves 1131 and 1141 are configured as tracks for maintaining the movement of cutting element 1150 in the proximal-distal direction as the cutting element is translated. In other words, grooves 1131 and 1141 keep cutting element 1150 aligned as it travels along the length of jaw members 1130, 1140. Further, a slot 1132, provided within groove 1131, is configured to house a retaining flange of cutting element 1150 while one or both of jaw members 1130, 1140 move to an open position, and while cutting element 1150 is translated. For example, slot 1132 is configured to house retaining flange 1156, and groove 1141 is configured to house a lower portion of cutting element 1150 while jaw members 1130 and 1140 are in a closed position. If cutting element 1150 is deployed while jaw members 1130 and 1140 are in an open position or clamped around a large bundle of tissue, cutting element 1150 can slip out of groove 1141, but remains aligned by virtue of cooperation or engagement between retaining flange 1156 coupled thereto, and slot 1132.

Further, each jaw member 1130, 1140 can be provided with one or more electrodes 1136 (or electric terminals) that deliver electrical energy for performing electrosurgical procedures. For example, end effector 1103 can be a tissue sealing and cutting end effector. To perform a sealing procedure, end effector 1103 is used to grasp tissue (such as, e.g., a vascular bundle or skeletonized vessel) or other material between upper and lower jaw members 1130, 1140, and apply electrical energy to the material via electrodes 1134, 1144. The electrical energy may be applied, for instance, using input controls at a surgeon's console of a teleoperated surgical system or otherwise from a generator source (ESU). The tissue may be grasped between working surfaces of jaw members 1130, 1140, as described in FIG. 4. The application of electrical energy at a specific voltage (and, in the case of A/C voltage, frequency) generates heat in the material due to the resistance inherent to the material. In the case of tissue, the heat causes the proteins within the grasped tissue to melt until they are crosslinked, thereby forming a permanent weld or seal. Polarities and amplitudes of voltage can be adjusted using a control panel at the ESU, or by a surgeon operating a console, or any other method. To cut the sealed material, cutting element 1150 is deployed from a proximal-most position (i.e. "garaged" position depicted in FIG. 11A) to a distal-most position (as depicted in FIG. 11B) by being translated along a length of grooves 1131 and 1141, i.e. in the proximal-distal direction.

In addition to sealing electrodes 1134, 1144, each jaw member 1130, 1140 further comprises plastic outer layers 1135, 1145, and insulating layers 1136 and 1146. Plastic outer layers 1135, 1145 are plastic overmold layers that retain electrodes 1134, 1144 respectively, and provide thermal isolation between each electrode and tissue surrounding end-effector 1103. Insulating layer 1136 is provided to electrically isolate metal body portion 1133 from electrode 1134, and insulating layer 1146 is provided to electrically isolate metal body portion 1143 from electrode 1144. Moreover, as grooves 1131 and 1141 and slot 1132 are provided within metal body portions 1133 and 1143 respectively, cutting element 1150 remains electrically isolated from electrodes 1136 and 1146 as it is translated along the slots. As described herein, cutting element 1150 and retaining flange 1156 may be electropolished to enable smooth translation along slot 1132. Further, inner walls of grooves 1131, 1141 and slot 1132 may be lined with plastic so as to provide less friction during translation. In some embodiments, retaining flange 1156 may also be made out of plastic. The plastic may comprise, for example, PPA™, or (PTFE) (e.g., Teflon™), and may be constructed by overmolding. Moreover, electrodes 1134 and 1144 may be manufactured from stainless steel, thereby maintaining uniform electrical conductivity and thermal properties.

Figure 12A:
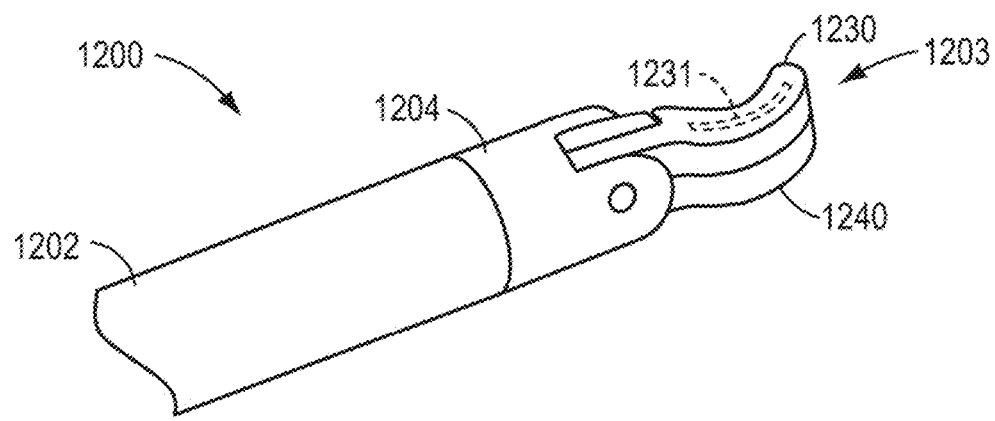
FIGS. 12A and 12B show perspective and top views of an exemplary embodiment of an electrosurgical end effector comprising a pair of curved gripping jaw members and a retaining slot in one of the jaw members.
Figure 12B:
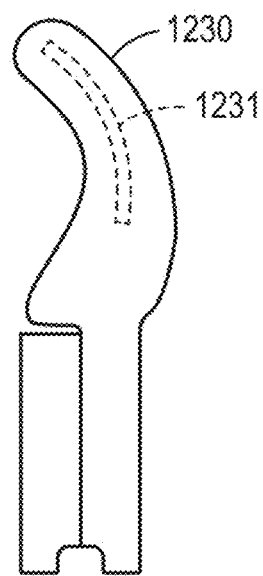

FIGS. 12A and 12B show perspective and top views of an exemplary embodiment of a surgical instrument 1200 having an end effector 1203 comprising a pair of curved gripping jaw members 1230, 1240 and a retaining slot 1231 in one of the jaw members. Gripping jaw members 1230, 1240 may be curved in order to provide enhanced visualization, access, and gripping abilities, particularly for instruments that lack a teleoperated wrist as described herein. Gripping jaw members 1230, 1240 may have a curved shape (curved longitudinal axis) along a lengthwise, proximal-distal direction of the jaw members 1230, 1240. Further, a groove and/or slot 1231 provided within one or both of jaw members 1230, 1240 is correspondingly curved, enabling a cutting element (not shown) with a flange attached therein to be translated in a direction along the curve of jaw members 1230, 1240. A cutting element drive component for translating the cutting element may be made of a flexible material to enable translation along the curved jaw members. In an exemplary embodiment, the instrument 1200 may be configured as an electrosurgical instrument with jaw members configured to delivery electrosurgical energy.

Various exemplary embodiments described herein enable a cutting element of a gripping end effector to be deployed and retracted without slipping out of alignment and engagement with one or more of the gripping jaws throughout the range of opening/closing motion of the jaws. Although the shape of the cutting element and retaining feature are respectively depicted as a generally vertically oriented plane and a laterally extending component perpendicular to the plane of the cutting element, other configurations and arrangements are contemplated as within the scope of the present disclosure and would be appreciated by those of ordinary skill in the art in view of the present disclosure. Nonlimiting exemplary configurations may include, for example, an L-shape or 7-shape, and corresponding retaining slots may be provided in either or both of the opposing jaw members, so long as the ability to retain the cutting element through a range of translation and over a substantial range of opening/closing motion of the jaws is maintained, and without compromising a structural strength of the jaw members. In some exemplary embodiments, a slot provided in a jaw member may extend through a body of the jaw member, for at least a portion of a length of the jaw member. This opening through a top of the end effector enables an operator such as, for instance, a surgeon, to monitor a deployment of a cutting element. To further enable this monitoring, the retaining feature may further comprise a vertical member extending through said extended slot, such that the deployment of the cutting element is visible from jaw member, thereby acting as an indicator of the position of the cutting element. In other words, a portion of the retaining flange can be transparent through the exterior of the jaw member to provide visibility to the complementary retaining feature or slot, and the retaining feature or flange that is translated therein.

Although the embodiments describe surgical procedures performed on materials such as tissue, for example, blood vessels, the surgical instruments described herein can also be used on materials having properties similar to tissue for training and/or testing purposes. Moreover, the principles described herein may be applied in other types of remotely-actuatable and/or robotic instruments used for a variety of applications, such as space technologies, manufacturing, oil/drilling, remote exploration, and so on. Further modifications and alternative embodiments will be apparent to those of ordinary skill in the art in view of the disclosure herein. Other configurations of cutting elements, retaining flanges, sharp or rounded edges, electrode placement, materials, shapes, relative dimensions etc. can be used and modified to achieve various desired effects. Further, the systems and the methods may include additional components or steps that were omitted from the diagrams and description for clarity of operation.

Accordingly, this description is to be construed as illustrative only and is for the purpose of teaching those skilled in the art the general manner of carrying out the present teachings. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the spirit and scope of the present teachings and following claims. The nature of information depicted in the figures and described herein is exemplary. Those persons having skilled in the art would appreciate modifications to the displays can be made, such as, for example, depending on the number and type of controls desired, the number and/or type of instruments to be used, and/or the functions of the instruments used and the type of fluxes supplied by flux supply units. The various instrument setups depicted in the drawings and described herein are exemplary in nature and the present disclosure contemplates other instrument setups. Moreover, it should be understood that the figures are not drawn to scale.

This description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly.

It is to be understood that the particular examples and embodiments set forth herein are nonlimiting, and modifications to structure, dimensions, materials, and methodologies may be made without departing from the scope of the present teachings. Other embodiments in accordance with the present disclosure will be apparent to those skilled in the art from consideration of the specification and practice of the invention disclosed herein. It is intended that the specification and examples be considered as exemplary only, with a scope of the following claims being entitled to their broadest interpretation, including equivalents.

What is claimed is:

1. A surgical instrument, comprising:
    a pair of jaw members configured to grip material, wherein a first jaw member of the pair of jaw members comprises
        a groove along a length portion of the first jaw member, the groove extending from a gripping surface of the first jaw member in a first direction; and
        a slot along the length portion of the first jaw member and extending from the groove in a second direction, the second direction being different than the first direction;
    a cutting element comprising a first edge engaged with the groove, the cutting element translatable along the groove; and
    a retaining feature coupled to the first edge of the cutting element and engaged with the slot,
    wherein the retaining feature remains engaged with the slot throughout a range of translation of the cutting element along the groove, and
    wherein the cutting element is translatable along the groove independently from a movement of the pair of jaw members between an open position and a closed position.

2. The surgical instrument of claim 1, wherein the pair of jaw members is coupled to a wrist configured to articulate in multiple degrees of freedom.

3. The surgical instrument of claim 2, further comprising a cutting element drive component configured to translate the cutting element along the groove.

4. The surgical instrument of claim 3, wherein the cutting element drive component is bendable in response to articulation of the wrist in the multiple degrees of freedom.

5. The surgical instrument of claim 3,
    wherein the cutting element comprises a second edge and a third edge, the second edge opposite from the first edge, the third edge extending between the first and second edges, and
    wherein the cutting element drive component is coupled to the third edge of the cutting element.

6. The surgical instrument of claim 5, wherein the cutting element comprises a fourth edge opposite from the third edge, the fourth edge comprising a sharpened edge configured to cut the material gripped by the pair of jaw members.

7. The surgical instrument of claim 3, wherein the cutting element drive component is routed through the wrist.

8. The surgical instrument of claim 7, wherein the cutting element drive component is routed through a center of the wrist.

9. The surgical instrument of claim 1, further comprising:
    a cutting element drive component configured to translate the cutting element along the groove,
    wherein the cutting element drive component is bendable in response to movement of the pair of jaw members between the open and closed positions.

10. The surgical instrument of claim 1, wherein the retaining feature and the cutting element are integral parts of a same piece of material.

11. The surgical instrument of claim 10, wherein the retaining feature and the cutting element are formed by machining or molding the piece of material.

12. The surgical instrument of claim 1, wherein the retaining feature and the cutting element are coupled together.

13. The surgical instrument of claim 12, wherein the retaining feature comprises a pin coupled to the cutting element.

14. The surgical instrument of claim 12, wherein the retaining feature is overmolded onto the cutting element.

15. The surgical instrument of claim 1, wherein each jaw member of the pair of jaw members is configured to be moved from an open position to a closed position independently from the other jaw member of the pair of jaw members.

16. The surgical instrument of claim 1,
    wherein a second jaw member of the pair of jaw members comprises a second groove along a length portion of a gripping surface of the second jaw member, and
    wherein a second edge of the cutting element, opposite from the first edge, is engageable with the second groove on condition of the pair of jaw members being in the closed position.

17. The surgical instrument of claim 16, wherein the second edge of the cutting element is disengaged from the second groove on condition of the pair of jaw members being moved out of the closed position.

18. The surgical instrument of claim 1, wherein at least one of the pair of jaw members comprises an electrode.

19. The surgical instrument of claim 1, wherein the gripping surface of the first jaw member comprises an electrode.

20. The surgical instrument of claim 1, wherein the first jaw member and the groove are curved in the length direction of the first jaw member.

* * * * *